United States Patent [19]

Sakurada et al.

[11] 4,176,070

[45] Nov. 27, 1979

[54] SEMI-PERMEABLE MEMBRANES OF REGENERATED CUPRAMMONIUM CELLULOSE AND METHOD FOR HEAT STERILIZATION THEREOF IN PHYSIOLOGICAL SALINE

[75] Inventors: Yutaka Sakurada, Kyoto; Kimihisa Sunahara, Saiki; Kazuhisa Yamauchi, Kyoto, all of Japan

[73] Assignees: Kuraray Co., Ltd.; Kawasumi Laboratories, Inc., both of Kurashiki, Japan

[21] Appl. No.: 886,949

[22] Filed: Mar. 15, 1978

[30] Foreign Application Priority Data

Mar. 18, 1977 [JP] Japan .................................. 52-30782
Oct. 27, 1977 [JP] Japan ................................ 52-130159
Nov. 14, 1977 [JP] Japan ................................ 52-137139

[51] Int. Cl.² ........................ A61L 1/00; B01D 13/04; B01D 39/18
[52] U.S. Cl. .............................. 210/500 M; 210/140; 210/321 B; 210/501; 422/38; 422/44; 422/48
[58] Field of Search ................................. 21/2, 56, 99; 210/500 M, 321 B, 22 R, 321 R, 140, 501; 422/1, 26, 38, 44, 48

[56] References Cited

U.S. PATENT DOCUMENTS

| | | | |
|---|---|---|---|
| 3,012,844 | 12/1961 | Screnock | 21/56 |
| 3,781,378 | 12/1973 | Kantor | 210/500 M |
| 3,841,492 | 10/1974 | Brinegar | 210/500 M |
| 3,864,289 | 2/1975 | Rendall | 210/500 M |
| 4,008,047 | 2/1977 | Petersen | 210/321 B |

OTHER PUBLICATIONS

"Dialysis Transplantation Nephrology;" Ed. Robinson et al.; vol. 13; pp. 242–249; 1976.
"Millipore;" Tech. Bulletin; 1961; pp. 1, 2, 4, 8 & 9.

*Primary Examiner*—Joseph Scovronek
*Assistant Examiner*—Bradley Garris
*Attorney, Agent, or Firm*—Barry Kramer

[57] ABSTRACT

Semi-permeable membranes of regenerated cellulose are subjected to wet-heat sterilization at a temperature of 105° to 140° C. During the treatment, the membranes are maintained in contact with an aqueous medium such as water or physiological saline. For the dialysis of body fluids, hollow fiber, semi-permeable membranes so sterilized exhibit a sonic modulus of at least $6.5 \times 10^{10}$ dynes/cm². Hollow fibers made of cuprammonium regenerated cellulose are particularly preferred for the above purpose.

7 Claims, 1 Drawing Figure

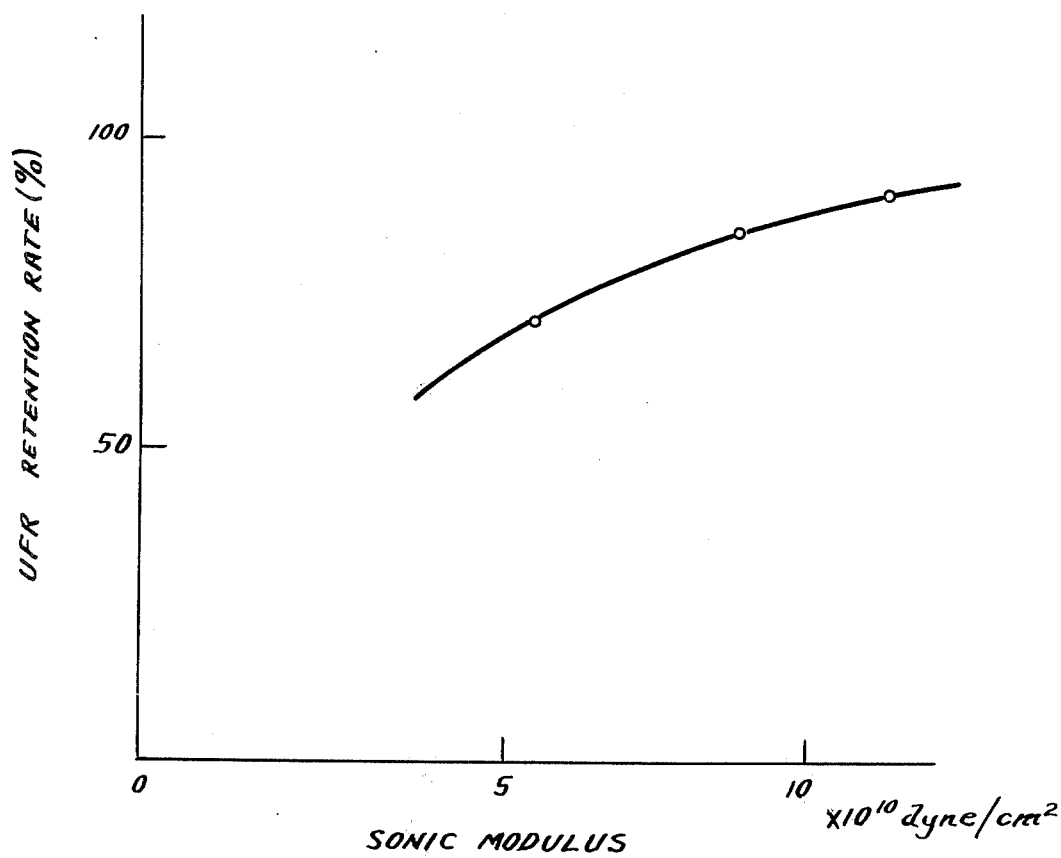

SEMI-PERMEABLE MEMBRANES OF REGENERATED CUPRAMMONIUM CELLULOSE AND METHOD FOR HEAT STERILIZATION THEREOF IN PHYSIOLOGICAL SALINE

BACKGROUND OF THE INVENTION

1. Field of the Invention

This invention relates to a method for sterilizing semi-permeable membranes, and to the sterilized membranes. More particularly, it relates to a method of wet-heat sterilization of a semi-permeable membrane of regenerated cellulose, and to the semi-permeable membranes so sterilized.

2. Description of the Prior Art

Membranes with a variety of configurations such as hollow fiber, tubing and flat sheet have been widely employed in the treatment of fluids. Typical use for such membranes are in apparatus for purifying body fluids such as blood, which remove endogenous metabolites and exogenous toxins from such fluids. The artificial kidney is an apparatus designed to purify the blood with use of such a membrane and the ascitic fluid treating apparatus employs such a membrane for filtration and/or concentration of accumulated ascitic fluid.

The membranes in such medical apparatus must be used strictly under sterile conditions. The methods heretofore proposed for the sterilization of membranes include sterilization by immersion in formalin, sterilization with ethylene oxide gas and sterilization by gamma-ray radiation. The formalin immersion and ethylene oxide gas sterilization techniques have been widely practiced. However, it has been found that the use of membranes sterilized by such known methods results in the absorption of residual formalin or ethylene oxide into the body fluids and, or repeated use of such membranes, such substances gradually accumulate in the body until, finally, a harmful level can be attained. Under the circumstances, the aforementioned radiation sterilization technique has been preferred, but the use of radiation has a risk of health hazards and, hence, requires complicated and costly equipment, thus presenting its own problems to be solved before such a technique may be well established. It is for this reason that a sterilizing technique safe to patients has long been desired and sought after.

SUMMARY OF THE INVENTION

It is an object of the present invention to provide a method for sterilizing a semi-permeable membrane characterized in that said semi-permeable membrane of regenerated cellulose is subjected to wet-heat treatment at a temperature within the range of 105° to 140° C.

It is another object of the present invention to provide a regenerated cellulose hollow fiber membrane suitable for use in an artificial kidney aparatus, which membrane exhibits a sonic modulus of at least $6.5 \times 10^{10}$ dynes/cm$^2$ and has been sterilized by wet-heat treatment within the range of 105° to 140° C.

It is still another object of the present invention to provide a method for sterilizing a regenerated cellulose hollow fiber, semi-permeable membrane characterized in that a cuprammonium cellulose hollow fiber having a sonic modulus of at least $6.5 \times 10^{10}$ dynes/cm$^2$ is sterilized by heating at a temperature of 105° to 140° C., while it is in contact with water or physiological saline.

BRIEF DESCRIPTION OF THE DRAWING

FIG. 1 is a graphic representation showing the correlation between UFR retention rate (%) and sonic modulus ($\times 10^{10}$ dynes/cm$^2$) of the hollow fiber membrane.

DETAILED DESCRIPTION OF THE INVENTION

The wet-heat sterilization method according to this invention is a method which is commonly used in the sterilization of other medical materials such as injection syringes, needles, surgical instruments and the like. However, it has never been suggested nor would it be expected that such practice could be applied to the sterilization of semi-permeable membranes as defined in the present invention. Thus, because of the special solute-permeation characteristics of membranes made of regenerated cellulose or other polymers, it is believed that their micro-structures are significantly different (possessing comparatively loose internal structures) from the internal structures of the shaped products intended for other uses, e.g., wrapping film.

For the above reason, it is known that the microstructure of such a membrane is unstable, delicate and vulnerable to severe conditions, being especially sensitive to heat. It is for this reason that, in the production of such a membrane and, for that matter, in any treatment preceding its use, extraordinary care is taken to ensure that the product will not be subjected to unduly high temperatures. In fact, the aforementioned conventional sterilization techniques have been developed and employed because they do not involve the use of a high temperature.

Against the above background, it has now been found that wet-heat treatment at 105° to 140° C. can be applied to the sterilization of polymeric membranes without impairing the solute-permeation and mechanical properties of membranes provided that the membranes are made of regenerated cellulose.

It has now been found in a study of the changes in such properties under wet-heat conditions that the permeability of such a regenerated cellulose membrane to substances such ar urea, acid, creatinine, vitamin $B_{12}$ (a model of middle molecular weight substances) was not substantially affected whilst, depending on the type of regenerated cellulose, its permeability to water was markedly impaired. It was surprising to find that the alteration in characteristics of a membrane was largely accounted for by a change in water permeability, with its permeability to other low to middle molecular weight substances being not adversely affected.

When a membrane is used in an artificial kidney unit, its water permeability is a factor as important as its dialyzing characteristics, and membranes with inadequate water permeability cannot be put to practical use even if they excel in other properties.

It has been found that conventional membranes of other known synthetic polymers such as polyvinyl alcohol, ethylene-vinyl alcohol copolymer, polyacrylonitrile, polymethyl methacrylate, polyamide and other synthetic polymers lose their solute-permeation properties when exposed to wet-heat treatment and, therefore, cannot be subjected to such a treatment. For instance, a technical brochure (published by Enka-Glanzstoff A.G.) on cuprammonium cellulose tubes and hollow fibers, which are examples of regenerated cellulose membrane products, refers to the importance of handling such regenerated cellulose membranes under the conditions of 23° C. and 50% R.H., with the admonition that severe temperature conditions deviating from the above should be avoided.

A correlation has been found to exist between the micro-structure of a membrane and the alteration in its properties caused by autoclaving. As a parameter determinant of the permeation performance of a semi-permeable membrane, the micro-structure as established by electron-microscopy has provided the basis for many theories and discussions as can be seen, for example, from U.S. Pat. No. 3,888,771. In view of the fact that the water permeability of a membrane depends on its micro-structure, it was thought initially that the change in the properties of the membrane could be explained on the basis of the aforementioned micro-structural parameter. Contrary to this preconception, it was found that this conventional parameter failed to provide any useful information on the true changes in structure of membranes.

It has now been found that the change in micro-structure of a regenerated cellulose hollow fiber membrane can be correlated with its sonic modulus.

The sonic modulus of a fiber, film strip or the like is determined from the pulse velocity (the velocity at which a pulse is propagated) and, being independent of the degree of crystallinity at temperatures below Tg, it is a measure of the overall degree of molecular orientation consisting of the degree of orientation of the crystalline region and that of the amorphous region (cf. Journal of Applied Polymer Science 3, 266,276 (1960)).

In accordance with this invention, a dry, hollow fiber membrane which has been allowed to stand at least overnight at 25° C. and 40% R.H. is subjected to the measurement of the velocity of propagation of pulses of 10 kilocycles by means of a KLH pulse propagation meter.

The sonic modulus Es of a test material is calculated from the sonic velocity C which can be determined by the above procedure and the density $\rho$ which can be determined by the conventional procedure, e.g. the density gradient method, using the following equation:

$$Es = \rho C^2$$

A hollow fiber of regenerated cellulose having an Es value of at least $6.5 \times 10^{10}$ dynes/cm$^2$ will suffer only a small reduction in water permeability when subjected to wet-heat treatment and is useful for the purpose of this invention. In contrast, a hollow fiber of regenerated cellulose having an Es value below $6.5 \times 10^{10}$ dynes/cm$^2$ will suffer a reduction of 25% or more in hydraulic permeability and has an absolute permeability value (UFR, ultrafiltration rate) which does not exceed $8 \times 10^{-2}$ ml/cm$^2$ atm. hr., thus being unusable in artificial kidney applications.

Although there is no critical upper limit to the sonic modulus of the membrane, it is preferably not higher than $18 \times 10^{10}$ dynes/cm$^2$ and, for still better results, not higher than $15 \times 10^{10}$ dynes/cm$^2$. If such upper limit is exceeded, the highly-oriented structure of the hollow fiber membrane would provide only a low dialyzing performance as well as low water permeability, thus making the membrane unusable as an artificial kidney membrane.

The regenerated cellulose membrane used according to this invention can be a membrane obtained by the regeneration of any cellulose derivative. Thus, for example, regenerated cuprammonium cellulose and saponified cellulose esters, e.g. cellulose di- or tri-acetate, can be successfully employed. The regenerated cellulose membranes which can be employed include the membranes formed in a tubular or flat shape by conventional techniques. These membranes are assembled, in the case of artificial kidneys for instance, in hollow-fiber, coil and kiil modules. While, normally, the regenerated cellulose membrane is subjected to said wet-heat treatment as previously assembled into a module, it is of course possible to so treat the membrane prior to assembling.

The hollow fiber of regenerated cellulose which is preferably employed in the practice of this invention is a fiber of regenerated cuprammonium cellulose which has a sonic modulus of at least $6.5 \times 10^{10}$ dynes/cm$^2$. Still more desirable is such a regenerated cellulose membrane having a sonic modulus of at least $7.7 \times 10^{10}$ dynes/cm$^2$. Other types of regenerated cellulose hollow fiber membranes, such as the saponified cellulose acetate hollow fiber membranes which are currently available on the market and the regenerated cellulose hollow fiber obtained from cuprammonium cellulose which exhibit a sonic modulus below $6.5 \times 10^{10}$ dynes/cm$^2$, cannot be made into efficient artificial kidney membranes by wet-heat sterilization. The saponified cellulose acetate commercially available today has a sonic modulus below $6.5 \times 10^{10}$ dynes/cm$^2$ and is unsuitable as aforesaid but, if it has been modified so as to give a higher sonic modulus, for example, by orienting the same to a high degree in the stage of cellulose acetate and, thereafter, saponifying the same, such regenerated cellulose can be successfully employed for the purposes of this invention.

It has now been discovered that the difference between the sonic moduli of such a membrane before and after the wet-heat treatment is comparatively small, differences being on the order of $2 \times 10^{10}$ dynes/cm$^2$, at most. It is, thus, to be understood that, if its sonic modulus before the wet-heat treatment does not meet the requirement of this invention, a membrane that would satisfy the present requirement after the treatment can be successfully utilized for the purposes of this invention.

Hollow fibers of regenerated cellulose having the desired sonic modulus can be manufactured, for instance, by adjusting the formulation of the spinning solution, conditions of coagulation and regeneration, conditions of stretching subsequent to the spinning stage, conditions of heat treatment and so forth. While these conditions can be varied rather widely, it is generally advantageous to set a majority of the conditions each within an easily maintainable range and vary one or two remaining conditions, such as the spinning draft ratio and/or wet-heat stretching ratio, so as to obtain the desired sonic modulus. Thus, a typical procedure can consist of attenuating the ordinary spinning dope in the air, passing it into an alkaline coagulation bath, stretching it between the coagulation bath and an acid regeneration bath at the rate of about 0 to 50%, rinsing the regenerated hollow fiber and drying the same.

The ultrafiltration rate (UFR) of the regenerated cellulose hollow fiber obtained according to this invention undergoes an extremely small reduction by wet-heat sterilization. As mentioned hereinbefore, the water permeability of ultrafiltration rate of a membrane is one of the basic parameters of artificial kidney performance and, if the UFR of a membrane is below a certain level, the membrane has no practical usefulness as an artificial kidney. When the difference between the UFR values before and after the wet-heat treatment of a regenerated cellulose hollow fiber membrane is expressed as a retention rate, the retention rate of the semi-permeable membrane of this invention is not less than 75% and, preferably, not less than 80%.

Thus, a membrane having a sonic modulus of at least $6.5 \times 10^{10}$ dynes/cm$^2$ has a UFR retention rate of at least 75% and a membrane having a sonic modulus of at least $7.7 \times 10^{10}$ dynes/cm$^2$ has a UFR retention rate not less than 80%. It is necessary that, after the wet-heat treatment, the membrane has a UFR value of at least $8 \times 10^{-2}$ ml/cm$^2$ atm.hr. while satisfying the above-mentioned retention rate requirement.

FIG. 1 is a graphic representation of the correlation between the sonic modulus and the UFR retention rate of the regenerated cellulose hollow fiber.

The wet-heat treatment according to this invention is carried out in the presence of water, preferably distilled water or physiological saline at an elevated temperature in the range of 105° to 140° C., preferably at a temperature from 110° to 130° C. This wet-heat treatment is carried out in an autoclave or any other suitable pressure-resistant equipment which can be sealed gas-tight. There is no particular limitation on the time of heating as long as it is sufficiently long to effect the necessary sterilization. The heat treatment is normally carried out for about 20 to 40 minutes. Because of the presence of heated steam, the wet-heat treatment features a ready release of heat and an efficient penetration of heat into intricate spaces, thus providing for effective sterilization effects.

The conventional wet-heat treatment is generally carried out by the following alternative procedures. One of the procedures comprises either heating the material to be sterilized in boiling water at 100° C. or heating the material as the latter is immersed in water at 105° to 140° C. as described above, while the third procedure comprises sterilizing the material with heated steam only. The influence such wet-heat treatments would have upon the performance characteristics of the membrane material was determined and it was found that there are significant and unexpected differences among the above three sterilizing techniques in terms of the permeation properties of the sterilized membrane as well as in the adaptability of the membrane to medical applications.

Thus, one of the differences is concerned with the change in hydraulic permeability as caused by a wet-heat treatment. In other words, the aforementioned correlation between sonic modulus and UFR retention holds true only with sterilization in water and, in the case of autoclaving with use of steam alone, the UFR of the membrane generally decreases so drastically as to make the membrane useless.

Another difference is that, compared with sterilization by said steam autoclaving, heat sterilization in an aqueous medium according to the present invention yields an improved dialyzing performance. In the case of steam autoclaving, the dialyzing performance has been found to be considerably affected. In this connection, it has been found that an artificial kidney unit incorporating the membrane of this invention displays a high dialysis performance in vivo which is 20 to 50% higher than the performance of the conventional artificial kidney unit sterilized with ethylene oxide gas. The improved performance thus obtained is currently believed to be attributable to a swollen structure imparted to the membrane by the application of the aforementioned conditions. It is currently believed that this swollen structure has not heretofore been obtained in semi-permeable membranes. Thus, it is quite surprising that whereas sterilization with steam alone considerably impairs the permeability characteristics of the membrane to make it unusable, wet-heat sterilization in water or physiological saline yields an excellent membrane performance even surpassing the best performance heretofore available.

The sterilizing treatment in boiling water at 100° C. entails the evolution of bubbles which adhere to the hollow fiber membrane. The air bubbles formed in the lumen of the fiber not only interferes with blood flow but tends to cause a clotting of blood. Therefore, the formation of air bubbles should be avoided as much as possible and such a treatment is undesirable as a method for sterilization artificial kidneys.

The wet-heat treatment according to this invention is preferably conducted in heatable and sealable equipment such as an autoclave.

Generally, since a regenerated cellulose membrane tends to become brittle on drying, a considerable amount of a plasticizer such a glycerin is incorporated. Therefore, notwithstanding the fear of substances being eluted from the membrane per se when the latter is used in an artificial kidney apparatus, it has been heretofore impossible to pursue the problem of elution from the membranes. In regard to an artificial kidney of the wet type, for example, there is the problem of elution of the formalin sterilant. In the case of the membrane and the sterilizing method according to this invention, wherein no such additive and sterilant are contained and the membrane is treated in water or physiological saline at above 105° C., any contaminants which are contained in the membrane and tend to elute during practical use thereof at a lower temperature, e.g. room temperature, than the said treating temperature, are almost completely removed beforehand.

Furthermore, a clinical evaluation of the membrane obtained by the treatment of this invention has shown that, compared with the membrane sterilized with ethylene oxide gas, it has less adverse effects upon the blood. Thus, such unexpected results as the reduced possibility of clotting and thrombus are obtained. All these results cannot be accomplished by heat sterilization employing steam autoclaving alone.

If the membrane treated by the present sterilizing method is cooled and sealed, it can be maintained in sterile condition. If necessary, after the sterilization treatment, aseptic replacement may be carried out with distilled water or physiological saline, and the product may then be kept sealed until used. Of course, it is possible to apply this membrane to an artificial kidney made of an appropriate material for such a treatment and the thus obtained module may be subjected to said wet-heat treatment. In the sterilizing method according to this invention, immersion in physiological saline is one of the preferred embodiments. Because physiological saline is isotonic with body fluids, it can be safely used in practical use. Where the elution from the membrane, potting agent and the like is considered to be a problem, it is preferable to carry out a preliminary heat treatment in water or physiological saline at 70° to 120° C., drain the membrane, reimmerse it in water or physiological saline and then carry out the sterilization treatment in the above manner. Since the module incorporating the membrane according to this invention contains only water or physiological saline, it is not necessary to rinse it to remove the sterilant before use and, particularly when the physiological saline has been employed, the module can be immediately put to use. The conventional membrane sterilized with formalin or ethylene oxide gas must be subjected to a preliminary rinse of about 30 minutes.

Thus, since the method described herein enables the complicated preparatory procedure required in the current dialytic therapy to be greatly simplified, the present invention provides considerable advantages in the biomedical and clinical fields.

The following examples are intended to further illustrate the present invention but are not intended to impose any limitations on the scope or spirit thereof. Unless otherwise stated, all parts and percentages are by weight.

EXAMPLE 1

A regenerated cellulose hollow fiber produced by the cuprammonium cellulose process (manufactured by Enka-Glanzstoff A.G.) was washed with ethanol to remove the isopropyl myristate contained herein, and was dried. The hydraulic permeability (UFR) of this membrane was found to be $19.1 \times 10^{-2}$ ml/cm$^2$ atm.hr. The sonic modulus of this membrane was $11.4 \times 10^{10}$ dynes/cm$^2$. Using an autoclave, the membrane immersed in physiological saline was heat-sterilized at 120° C. for 20 minutes. The UFR of the sterilized membrane was $17.1 \times 10^{-2}$ ml/cm$^2$ atm.hr. and its UFR retention was 89.5%. The Es value of the membrane was $10.7 \times 10^{10}$ dynes/cm$^2$.

EXAMPLE 2

A regenerated cellulose hollow fiber manufactured by the cuprammonium cellulose process was rinsed with distilled water and dried. The sonic modulus and UFR of the dry membrane were $8.99 \times 10^{10}$ dynes/cm$^2$ and $14.4 \times 10^{-2}$ ml/cm$^2$ atm.hr., respectively.

This membrane was sterilized under wet-heat conditions as in Example 1. The UFR and sonic modulus of the sterilized fiber were $12.2 \times 10^{-2}$ ml/cm$^2$ atm.hr. and $9.24 \times 10^{10}$ dynes/cm$^2$, respectively. The UFR retention was 85%.

CONTROL EXAMPLE 1

A regenerated cellulose hollow fiber produced by the resaponification of cellulose acetate and having a sonic modulus of $5.53 \times 10^{10}$ dynes/cm$^2$ (manufactured by Cordis-Dow Co. ) had a measured UFR value of $9.83 \times 10^{-2}$ ml/cm$^2$ atm.hr. This hollow fiber was sterilized under wet-heat conditions as described in Example 1. The UFR and sonic modulus of the sterilized fiber were $6.84 \times 10^{-2}$ ml/cm$^2$ atm.hr. and $5.77 \times 10^{10}$ dynes/cm$^2$, respectively. The UFR retention of this membrane was 70%. The membrane was unsuitable for use as an artificial kidney.

CONTROL EXAMPLE 2

A hollow fiber as used in Example 1 was washed with ethanol, dried and sterilized in an autoclave using heated steam at 120° C. for 20 minutes. The UFR of the sterilized membrane was $3.92 \times 10^{-2}$ ml/cm$^2$ atm.hr.

EXAMPLE 3

A hollow fiber as used in Example 1 was washed with ethanol, dried and assembled into a cylindrical polycarbonate housing to fabricate a hollow fiber dialyzing module. The module was filled with distilled water and sterilized in an autoclave at 120° C. for 20 minutes. After it was confirmed to meet artificial kidney standards, the following clinical trial was carried out in the routine manner.

Case: female, 36 years of age, with chronic renal failure. Before dialysis, BUN 138.0 mg/dl, creatinine 10.0 mg/dl and uric acid 12.0 mg/dl. After 5 hours of dialysis, BUN 28.9 mg/dl, creatinine 3.4 mg/dl and uric acid 2.9 mg/dl were obtained. The rates of removal were 79.1%, 66.0% and 75.2%, respectively. Thus, the membrane was found to have an excellent dialysis performance.

CONTROL EXAMPLE 3

A hollow fiber washed with ethanol and dried, which was the same fiber as used in Example 3, was assembled into a module and sterilized with ethylene oxide gas. This module was tested in the same clinical trial as described in Example 3. The rates of removal were 50.5% for BUN, 47.6% for creatinine and 57.4% for uric acid.

EXAMPLE 4

An artificial kidney module fabricated in the same manner as Example 3 was filled with physiological saline and heat-treated in an autoclave at 120° C. for 20 minutes. After cooling, the saline was aseptically replaced with fresh physiological saline and the module was sterilized in the autoclave at 120° C. for 20 minutes. This sterilized product was used in a dialysis trial. Whereas, the amount of elution from the hollow fiber just washed with ethanol and dried and thereafter treated in water at 70° C. for 60 minutes was 8.3 ml (the consumption of potassium permanganate), the amount of elution from the hollow fiber after the abovementioned wet-heat sterilization was reduced to 0.20 ml.

What is claimed is:

1. A method for sterilizing a semi-permeable membrane of regenerated cuprammonium cellulose which comprises subjecting said semi-permeable membrane to heat treatment at a temperature of 105° to 140° C. in the presence of physiological saline.

2. A method as set forth in claim 1 wherein said heat treatment is conducted at a temperature in the range of 110° to 130° C.

3. A method as set forth in claim 2 wherein said semi-permeable membrane is a hollow fiber membrane.

4. A method as set forth in claim 1 wherein the membrane is preliminarily heat treated in physiological saline at a temperature of from 70° to 120° C.

5. A method as set forth in claim 4 wherein the second heat treatment is conducted at a temperature of 110° to 130° C.

6. A hollow fiber membrane of regenerated cuprammonium cellulose which has a sonic modulus of at least $6.5 \times 10^{10}$ dynes/cm$^2$ and has been sterilized at a temperature of 105° to 140° C. in the presence of physiological saline.

7. A sterilized fiber membrane as set forth in claim 6 immersed in sterile physiological saline contained in a housing.

* * * * *